(12) United States Patent
Takahashi et al.

(10) Patent No.: US 6,977,670 B2
(45) Date of Patent: Dec. 20, 2005

(54) METHOD AND APPARATUS FOR SELECTIVE REGISTRATION OF ENDOSCOPES WITH DATABASE

(75) Inventors: Tadashi Takahashi, Saitama-ken (JP); Makoto Koike, Tokyo (JP)

(73) Assignee: PENTAX Corporation, Tokyo (JP)

( * ) Notice: Subject to any disclaimer, the term of this patent is extended or adjusted under 35 U.S.C. 154(b) by 245 days.

(21) Appl. No.: 10/254,679

(22) Filed: Sep. 26, 2002

(65) Prior Publication Data
US 2003/0063188 A1   Apr. 3, 2003

(30) Foreign Application Priority Data
Sep. 28, 2001   (JP)   ............................ 2001-299978

(51) Int. Cl.[7] .............................................. H04N 7/18
(52) U.S. Cl. ............................. 348/65; 348/66; 348/67
(58) Field of Search .................................... 348/65–76

(56) References Cited

U.S. PATENT DOCUMENTS

| 6,181,368 | B1 | 1/2001 | Takahashi et al. |
| 6,322,496 | B1 | 11/2001 | Iida et al. |
| 6,322,497 | B1 * | 11/2001 | Takahashi ................... 600/118 |
| 6,436,032 | B1 * | 8/2002 | Eto et al. ................... 600/117 |

* cited by examiner

Primary Examiner—Andy Rao
(74) Attorney, Agent, or Firm—Greenblum & Bernstein, P.L.C.

(57) ABSTRACT

An electronic endoscope system includes an electronic endoscope and a processor to which the electronic endoscope is connectable. The processor includes a signal processor for displaying the images captured by the electronic endoscope, while adjusting the color balance thereof, and a memory holding an endoscope database. The processor further includes a CPU that retrieves endoscopic information from a memory of the electronic endoscope, which includes compensation data for white balance adjustment of the processor. The CPU registers the electronic endoscope with the endoscope database by storing the retrieved endoscopic information into the endoscope database when the white balance readjustment of the processor is required.

16 Claims, 7 Drawing Sheets

| register no. | scope name | serial no. | white balance | | registered date & time | used date & time | counter |
| --- | --- | --- | --- | --- | --- | --- | --- |
| | | | wb(r) | wb(b) | | | |
| 1 | FG-28A | 525813 | +4 | +5 | 971213.1313 | 001016.0913 | 159 |
| 2 | FC-34B | 631426 | +16 | +12 | 971213.1326 | 001014.1039 | 283 |
| 3 | FS-34A | 856339 | +1 | −9 | 971213.1339 | 991230.1513 | 229 |
| 4 | FC-27A | 297813 | −3 | +3 | 001015.0924 | 001016.1712 | 3 |
| 5 | FD-32A | 646526 | 0 | +2 | 971213.1413 | 000908.0839 | 145 |
| ... | ... | ... | ... | ... | ... | ... | ... |
| 38 | FG-21A | 790526 | +10 | +6 | 000913.0826 | 001018.1113 | 13 |
| 39 | FC-29A | 693639 | −2 | −5 | 001018.0839 | 001018.1426 | 26 |

FIG. 2

METHOD AND APPARATUS FOR SELECTIVE REGISTRATION OF ENDOSCOPES WITH DATABASE

BACKGROUND OF THE INVENTION

The present invention relates to an apparatus having an endoscope database, and more particularly, to an apparatus that selectively registers endoscopes with the database.

An electronic endoscope system generally includes an endoscope which captures images inside a human body with a solid state imaging sensor such as a CCD, and an endoscope processor for converting the output signal of the solid state imaging sensor into a video signal while adjusting the color balance of the captured image.

Generally, the electronic endoscope is equipped with a memory such as an EEPROM which holds type and serial number of the endoscope as well as compensation data for white balance adjustment of the endoscope processor. When the electronic endoscope is connected to the endoscope processor for the first time, the endoscope processor reads the white balance compensation data from the EEPROM for adjusting the color balance of the captured image.

Since the color balance of the image is affected by the property of the circuitry of the endoscope processor, the endoscope processor modifies the white balance compensation data obtained from the endoscope in accordance with the property of its circuitry and adjusts the color balance of the image based on the modified compensation data.

The endoscope processor is equipped with a memory in which an endoscope database is constructed. The endoscope processor registers, with the endoscope database, the modified compensation data in association with the type and the serial number of the endoscope. When the same endoscope is connected again, the white balance of the endoscope processor is adjusted based on the modified compensation data stored in the endoscope database.

The conventional endoscope processor, however, registers the information of the endoscope, i.e. white balance compensation data, type, serial number and so on, with the database whenever a new endoscope is connected thereto, irrespective whether or not the endoscope is utilized in actual diagnosis. Therefore, the conventional endoscope processor tends to fill up the database with the information of only temporarily connected endoscopes and the database becomes not able to record information of endoscopes that are connected thereto for practical use.

For the foregoing reasons, there is a need for an endoscope processor which does not register endoscopes, with the database, that are only temporarily connected thereto and therefore not practically used.

SUMMARY OF THE INVENTION

The present invention is advantageous in that it provides a method and an apparatus that selectively register electronic endoscopes that are supposed to be practically used with an database.

According to an aspect of the invention, there is provided an apparatus for processing an image captured by an electronic endoscope. The apparatus comprises a memory operable to store an endoscope database, a first processor that processes the image captured by the electronic endoscope, and a second processor that registers the electronic endoscope connected to the apparatus with the endoscope database. The second processor registers the electronic endoscope when an operational condition of the apparatus satisfies a predetermined condition. Therefore, the consumption of the endoscope is reduced in the apparatus arranged as above.

In some cases, the first processor displays the image captured by the electronic endoscope on a monitor. In such cases, the predetermined condition may include receipt of a requirement for executing white balance readjustment of the first processor. Since such adjustment is generally required when it is intended to practically use the image captured by the electronic endoscope, the apparatus arranged as above can selectively register electronic endoscopes, with the database, that are supposed to be practically used.

In other cases, the predetermined condition may include connection of the electronic endoscope with the apparatus for more than a predetermined period of time so that registration of endoscopes that are only temporarily connected to the processor and therefore supposed to be not practically used can be prevented.

Optionally, when all records of the endoscope database are already filled with data, the second processor may select one of records of the endoscope database and registers the electronic endoscope by replacing old data on the selected record with new data related to the electronic endoscope. In such way, the apparatus can ensure the registration of new data of the electronic endoscope even if the database is filled with old data.

BRIEF DESCRIPTION OF THE ACCOMPANYING DRAWINGS

FIG. 2 shows an exemplary structure of the endoscope database constructed on a memory of the electronic endoscope system of FIG. 1;

DETAILED DESCRIPTION OF THE EMBODIMENTS

Hereinafter, an embodiment of the invention will be described with reference to the accompanying drawings.

Figure 1:
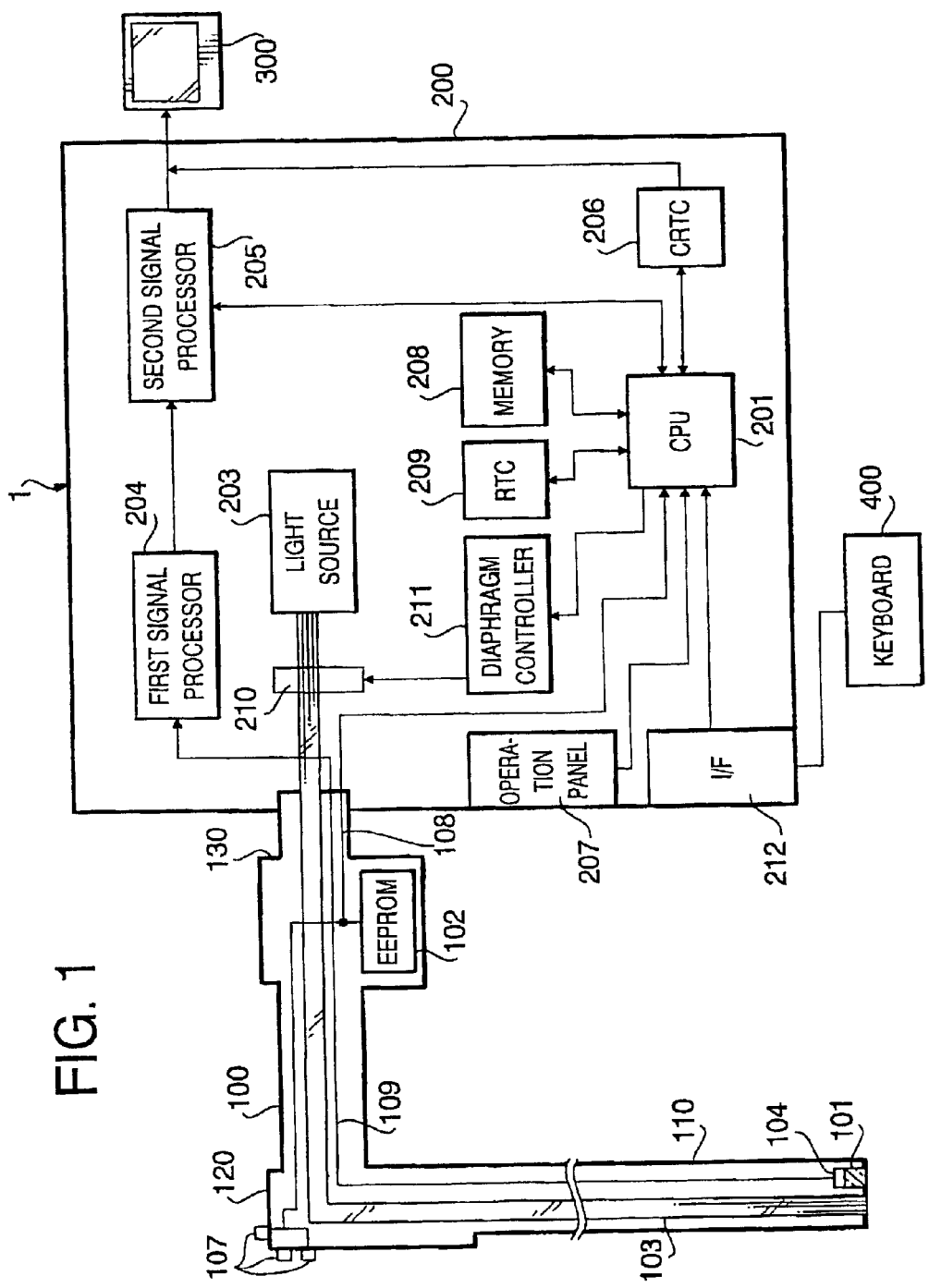
FIG. 1 is a schematic block diagram of an electronic endoscope system according to an embodiment of the invention.

FIG. 1 is a schematic block diagram of an electronic endoscope system according to an embodiment of the invention.

The electronic endoscope system 1 includes an electronic endoscope 100 and a processor 200 for processing electronic signals outputted from the electronic endoscope 100.

The electronic endoscope 100 includes a flexible inserting tube 110, an operation unit 120 connected to the proximal end of the inserting tube 110, and a connector 130 detachably connected to the processor 200.

A solid state imaging device such as a CCD 104 and an objective optical system 101 for forming an optical image on a light receiving surface of the CCD 104 are provided to the distal end portion of the inserting tube 110. A light guide 103 is inserted through the endoscope 100 from the connector 130 to the tip end of the inserting tube 110 to transmit light for illuminating the observing area of the CCD 104.

One or more operation buttons 107 are provided to the operation unit 120 for controlling the operation of the endoscope 100 and/or the processor 200. A memory 102 such as an EEPROM is provided to the electronic endoscope 100 at the connector 130. The EEPROM 102 holds data intrinsic to the endoscope 100, in which the EEPROM 102 is provided, such as type and serial number of the endoscope 100 as well as data for white balance the image captured by the CCD 104.

The processor 200 includes a CPU 201 which is connected to the operation buttons 107 and the EEPROM 102 via one or more signal cables 108. The CPU 201 controls the operations of the electronic endoscope 100 and the processor 200 in accordance with the signals from the operation buttons 107. The CPU 201 also accesses the EEPROM 102 to retrieve data stored therein.

The CPU 201 is further connected to an external input device such as a keyboard 400, via an interface 212, to control the operations of the endoscope 100 and the processor 200 in accordance with the commands inputted through the keyboard 400.

The processor 200 is also provided with an operation panel 207. A plurality of operation buttons (not shown) are arranged on the operation panel 207. An operator of the endoscope system 1 can press each button to control the operations of the endoscope 100 and the processor 200.

The processor 200 includes a light source 203 optically connected to an end of the light guide 103 for providing illuminating light thereinto.

A diaphragm 210 is provided on the light path of the light emitted from the light source 203 to restrict the amount of light introduced into the light guide 103. A diaphragm controller 211 controls the opening size of the diaphragm 210, or the amount of light introduced into the light guide 103, in accordance with signals from the CPU 201. The operator can freely control the opening size of the diaphragm 210 by operating the keyboard 400 or the operation panel 207.

First and second signal processors 204 and 205 are provided to the processor 200 to display images captured by the CCD 104 on a monitor 300. The first signal processor 204 receives the signal from the CCD 104 via a CCD signal cable 109 and transforms it into RGB digital image data representing the captured image in 256 levels of gray scale. The second signal processor 205 generates a video signal, such as NTSC, based on the digital image data from the first signal processor 204. The second signal processor 205 also adjusts the white balance of image represented by the video signal. The second signal processor 205 outputs the video signal to the monitor 300 so that the monitor 300 displays the image captured by the CCD 104.

Note that the output device to which the second signal processor 205 is connected is not limited to the monitor 300. The second signal processor 205 may also be connected to other kinds of output devices such as a video printer, for example.

A CRT controller (CRTC) 206 is provided to the processor 200 to superimpose text information on the image displayed on the monitor 300. The CRT controller 206 generates video signals representing the text information requested by the CPU 201 and output the video signals to the monitor 300 in synchronization with the video signal from the second signal processor 205. In this way, the processor 200 superimposes arbitrary text information, such as information obtained from the EEPROM 102, on the image captured by the CCD 104.

The processor 200 is also provided with a Real Time Clock (RTC) 209 and a memory 208. The RTC 209 provides information indicative of current date and time to the CPU 201. The memory 208 is a nonvolatile memory and holds an endoscope database with which information related to endoscopes are registered.

FIG. 2 shows an exemplary structure of the endoscope database constructed on the memory 208. The endoscope database includes thirty-nine records, which are assigned to different endoscopes. Thus, the thirty-nine endoscopes can be registered with the endoscope database at maximum. Each record includes items of "register no.", "scope name", "serial no.", "white balance (R gain, B gain)", "registered date & time", "used date & time" and "counter".

The item "register no." is utilized for identifying each record. In the present embodiment, serial numbers of 1 through 39 are assigned to the records.

The items "scope name" and "serial no." respectively hold data on the type and serial number of the electronic endoscope 100. When the endoscope 100 is connected to the processor 200, the type and the serial number of the endoscope 100 are retrieved from the EEPROM 102, and then stored in "scope name" and "serial no." of the endoscope database if a predetermined condition is satisfied as will be described later.

Sub-items "wb(r)" and "wb(b)" of the item "white balance" respectively represent the compensation values of the red and blue color gains of the second signal processor for the white balance adjustment thereof. Both "wb(r)" and "wb(b)" take a value between −128 and 127. In FIG. 2, the "R gain" and "B gain" of the fourth record are −3 and +3, respectively. This indicates the brightness of red color should be decreased by three levels in gray scale, while the brightness of blue should be increased by three levels.

The item "registered date & time" is the date and time when the electronic endoscope 100 is registered with the endoscope database. The item "registered date & time" includes six digits of date information and four digits of time information delimited by a period. If "registered date & time" is set to "971213.1313", for example, then it represents Dec. 13, 1997, 1:13 p.m. and if it is set to "001015.0924", then it represents Oct. 15, 2000, 9:24 a.m.

The item "used date & time" is the date and time when the electronic endoscope 100, identified by the "scope name" and the "serial no." on the same record, was connected to the processor 200 or used for the last time. The format of "used date & time" is the same as that of "registered date & time".

The item "counter" is the number of times the electronic endoscope 100 identified by the "scope name" and the "serial no." of the same record is connected to the processor 200.

When the main switch is turned on, the processor 200 is initialized. Then, the CPU 201 executes programs stored in the memory 208. In the present embodiment, the programs executed by the CPU 201 include "WHITE BALANCE READJUSTMENT ROUTINE", "ENDOSCOPE REGISTRATION ROUTINE", "USED DATE UPDATING ROUTINE" and "TIME DISPLAYING ROUTINE". The CPU 201 executes these programs in parallel.

The "WHITE BALANCE READJUSTMENT ROUTINE" readjusts the compensation value "wb(r)" and "wb(b)" stored in the endoscope database in accordance with a requirement from a user. The "ENDOSCOPE REGISTRATION ROUTINE" registers data of a new endoscope with the endoscope database. The "USED DATE UPDATING ROUTING" updates the "used date & time" of the endoscope database. The "TIME DISPLAYING ROUTINE" displays the current time on the monitor 300.

The four routines above utilize variables Current_Scope and Register_OK as global variables.

The variable Current_Scope is set to one of the integers of −1 through 39. Current_Scope=0 indicates that no endoscope is currently connected to the processor 200. Current_Scope=−1 indicates that the endoscope currently connected to the processor 200 is not yet registered with the endoscope database. If the variable Current_Scope is one of 1 through 39, in the present embodiment, it indicates that the data of the endoscope 100 currently connected to the processor 200 is recorded on the record of the endoscope database of which "register no." is same as the variable Current_Scope.

The variable Register_OK holds either of "True" and "False". Register_OK="True" indicates that the data of the endoscope 200 currently connected to the processor 200 should be registered with the endoscope database, while Register_OK="False" indicates the endoscope should not be registered.

Note that variables Current_Scope and Register_OK are set to "0" and "False", respectively, during the initialization process of the processor 200.

Figure 3:
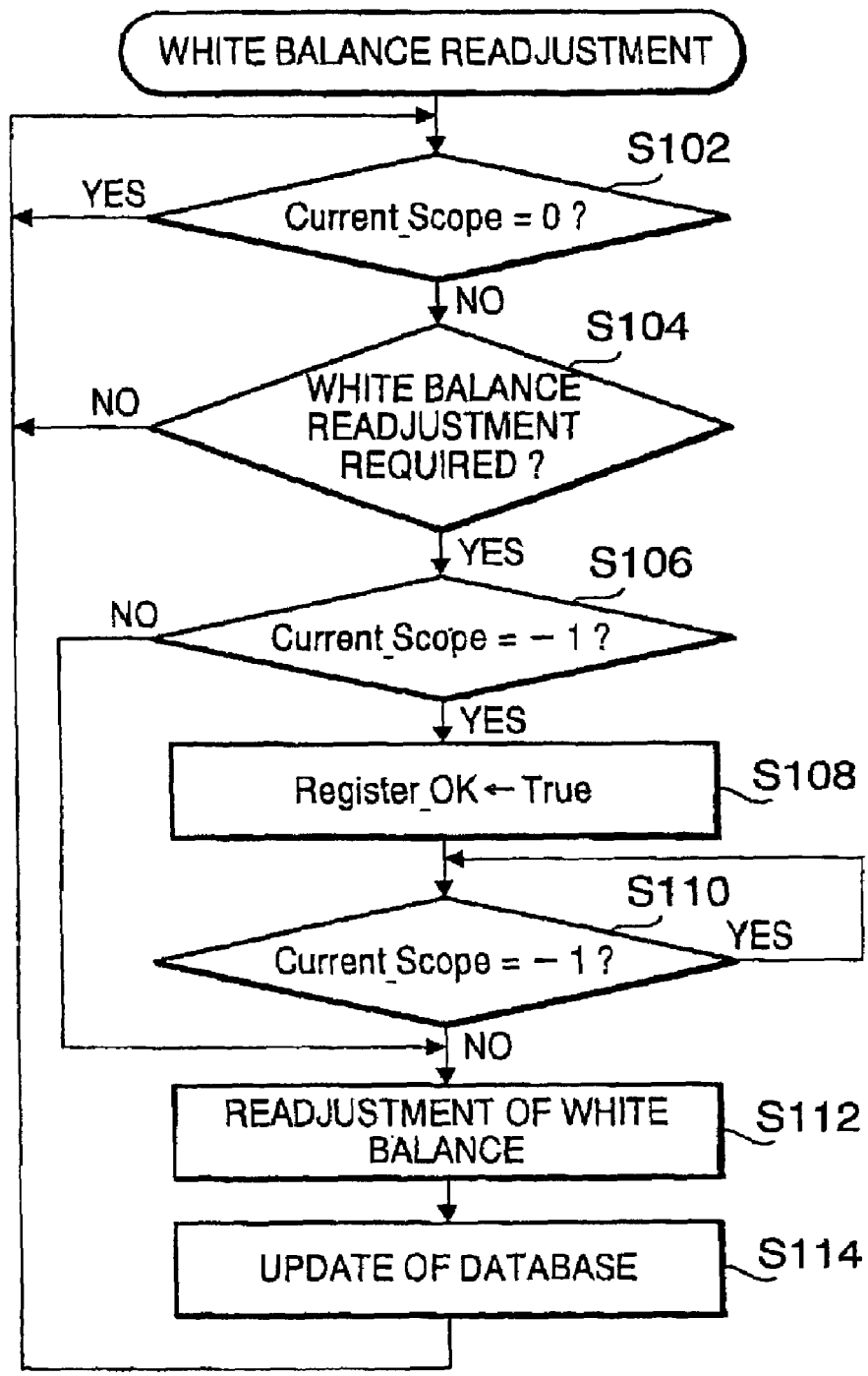
FIG. 3 is a flow chart showing the WHITE BALANCE READJUSTMENT ROUTINE.

FIG. 3 is a flow chart showing the WHITE BALANCE READJUSTMENT ROUTINE. In the first step S102 of this routine, it is determined whether an endoscope is connected to the processor 200 by checking the variable Current_Scope. This step is repeated until the variable Current_Scope becomes to hold a numeral other than "0" (S102:YES) since Current_Scope=0 indicates that no endoscope is currently connected to the processor 200.

If the variable Current_Scope becomes to hold a numeral other than "0", then it is determined whether there is a request for white balance readjustment (S104). This step is performed by checking whether a predetermined button of the control panel 207 is pressed or a predetermined command is inputted through the keyboard 400. If it is determined that the white balance readjustment is not requested (S104: NO), then control returns to step S102. If the white balance readjustment is requested (S104: YES), then control proceeds to step S106.

In step S106, it is determined whether the variable Current_Scope is "−1" or not. If the variable Current_Scope is "−1", which indicates the currently connected endoscope 100 is not yet registered with the endoscope database, control proceeds to steps S108 and S110 (S106:YES), otherwise control skips to step S112 (S106: NO).

In step S108, the variable Register_OK is set to "True". This allows the ENDOSCOPE REGISTRATION ROUTINE, which will be described later, to register the data of the currently connected endoscope 100 with the endoscope database 208 and set the variable Current_Scope to the "register no." of the record on which the data of the endoscope is stored.

In step S110, the WHITE BALANCE READJUSTMENT ROUTINE waits until the variable Current_Scope is set to a number except "−1" by the ENDOSCOPE REGISTRATION ROUTINE and then proceeds to step S112.

In step 112, the readjustment of the white balance is performed by taking the properties of the second signal processor 205 into account. That is, the CPU 201 monitors the RGB color signals outputted from the second signal processor 205, when a white color image is captured by the CCD 104, and adjusts both red color and the blue color compensation values of the second signal processor 205 so that the level of the output signals of red, green and blue colors becomes equal.

Then, in step S114, the red color and the blue color calibration values determined in step S112 are respectively stored in "wb(r)" and "wb(b)" of the record of which "register no." is the same as the variable Current_Scope. After step S114, control returns to step S102.

As described above, the WHITE BALANCE READJUSTEMNT ROUTINE sets the variable Register_OK to "True", which allows the ENDOSCOPE REGISTRATION ROUTINE to register the data of the currently connected endoscope with the endoscope database, when the white balance readjustment is required. Accordingly, if a new endoscope is connected to the processor 200 only temporarily and the white balance readjustment is not requested, then the data of this endoscope will not be registered with the endoscope database.

Figure 4A:
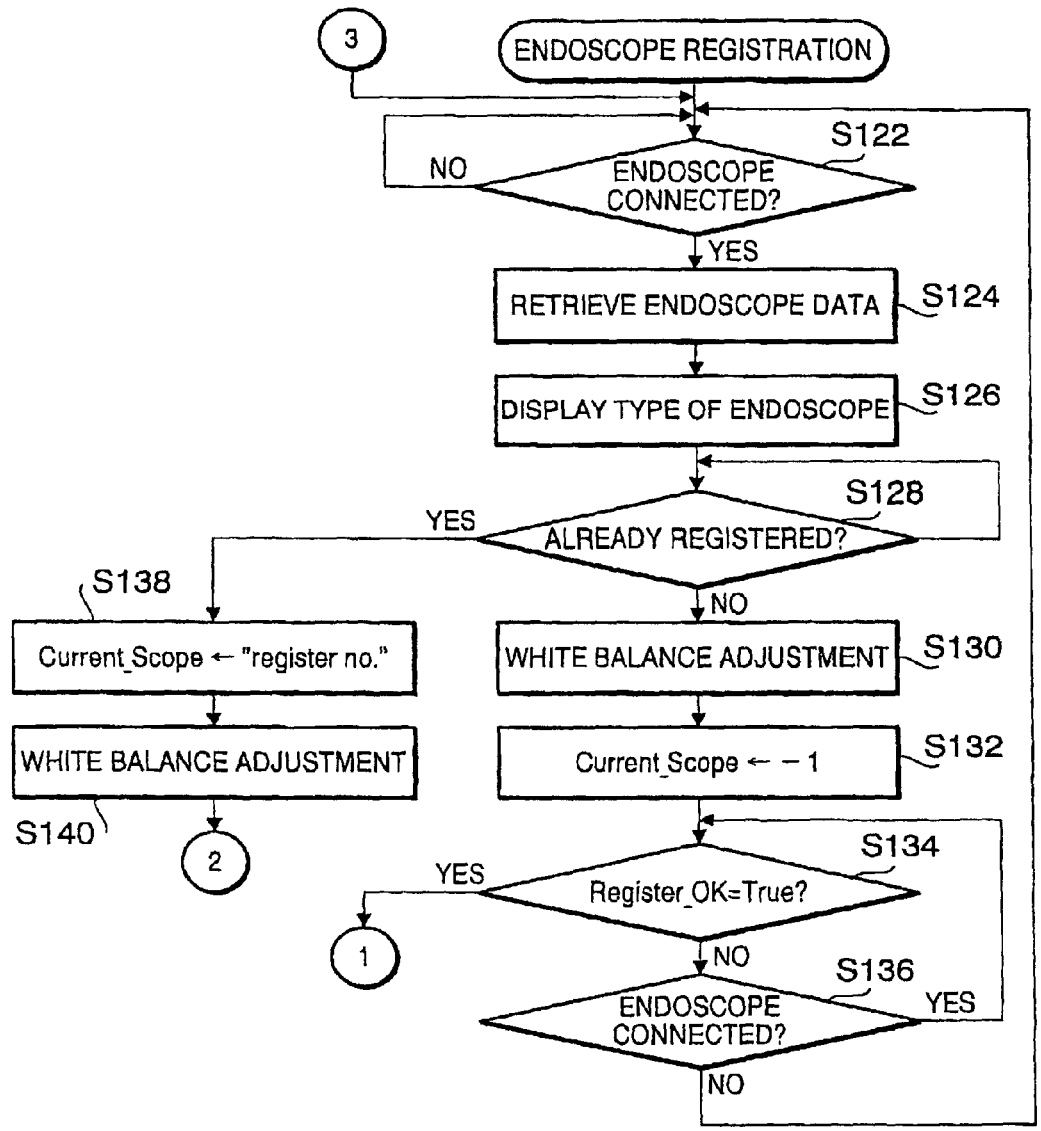
FIGS. 4A and 4B show a flow chart of the ENDOSCOPE REGISTRATION ROUTINE.
Figure 4B:
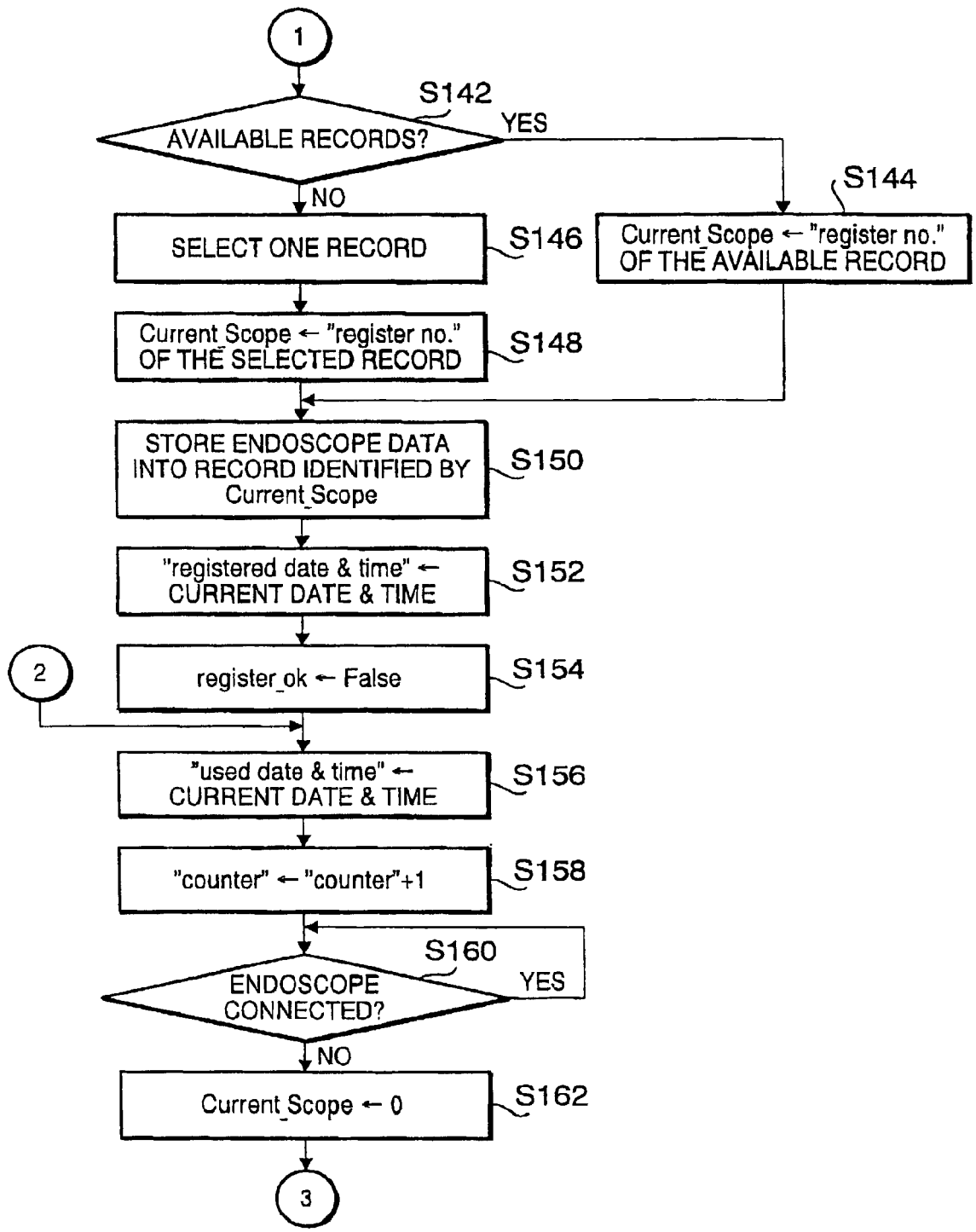

FIGS. 4A and 4B show a flow chart of the ENDOSCOPE REGISTRATION ROUTINE. In step S122 of the ENDOSCOPE REGISTRATION ROUTINE, the CPU 201 waits until the endoscope 100 is connected to the processor 200 (S122: NO). If the endoscope 100 is connected (S122: YES), then the CPU 201 retrieves the data held in the EEPROM 102 of the endoscope 100, i.e. the type and serial number of the endoscope 100 and the compensation values wb(r) and wb(b) for white balance adjustment of the second signal processor 205 (S124).

Next, the CPU 201 controls the CRTC 206 and thereby displays a character set on the monitor 300 that indicates the type of the currently connected endoscope 100 (S126).

In step S128, it is determined whether or not the currently connected endoscope 100 is already registered with the endoscope database by comparing the data retrieved from the endoscope 100 in step S124 with the data already stored in the endoscope database. If the database includes a record of which "scope name" and "serial no." are the same as the type and serial number obtained in step S124, then it is determined the endoscope 100 currently connected is one already registered (S128: YES). In this case, control proceeds to step S138. Otherwise, it is determined that the endoscope currently connected is not yet registered with the endoscope database and step S130 is performed.

In step S130, the CPU sends the compensation values wb(r) and wb(b) obtained in step S124 to the second signal processor 205 so that the white balance of the second signal processor 205 is adjusted based on these compensation values.

Next, the variable Current_Scope is set to "−1" to indicate that the currently connected endoscope 100 is not yet registered with the endoscope database (S132).

Next, it is determined whether the variable Register_OK is "True" or not (S134). In other words, it is determined whether or not the readjustment of white balance is requested for the currently connected endoscope 100.

Step S134 is repeated until the registration of the currently connected endoscope 100 is requested (S134: YES) or the endoscope 100 is disconnected from the processor 200 (S136: NO).

If the endoscope 100 is disconnected from the processor 200 (S136: NO), the process of the ENDOSCOPE REGISTRATION ROUTINE returns to step S122 without registering the data of the endoscope 100 with the endoscope database.

If it is judged that the variable Register_OK is "True" in step S134 (S134: YES), then it is determined whether there are any available records (records having no data except for "register no.") in the endoscope database (S142) as shown in FIG. 4B.

If there is an available record, then "register no." of the available record is given to the variable Current_Scope (S144). If there are more than one available records, the smallest "register no." of the available records is selected and given to the variable Current_Scope.

If there is no available record (S142: NO), one of the records in the endoscope database is selected based on the content of "registered date & time" of each record (S146). In the present embodiment, the record having the oldest "registered date & time" is selected. Then, the "register no." of the selected record is substituted to the variable Current_Scope (S148).

After steps S146 and S148, or after step S144, the data retrieved from the EEPROM 102 at step S124, i.e. the type and serial number of the endoscope 100 and the calibration values for white balance adjustment, are stored in the record of which "register no." is same as the variable Current_Scope (S150).

Next, the current date and time obtained from the RTC 209 are stored in "registered date & time" of the record of which "register no." is same as the variable Current_Scope (S152). Thus, the registration data and time of endoscope is recorded.

Next, the variable Register_OK is set to "False" (S154) so that the subsequently connected endoscope would not be registered before the readjustment of the white balance is required for that endoscope.

Referring back to step S128, if it is determined in this step that the currently connected endoscope 100 is already registered with the endoscope database (S128: YES), then control proceeds to step S138. In step S138, the "register no." of the record of which "scope name" and "serial no." coincides with the type and serial number retrieved from the endoscope 100 in step S124 is given to the variable Current_Scope (S138).

Next, the compensation values for white balance, wb(r) and wb(b), retrieved from the record mentioned above is given to the second signal processor 205 in order to balance the second signal processor for white color (S140).

After step S140 or S154, the data of "used date & time" of the record of which "register no." is same as the variable Current_Scope is updated (S156) by replacing the data thereof with the latest date and time information obtained from the RTC 209. Thus, the latest date and time when the endoscope is used is recorded.

Next, "counter" of the same record is also updated by incrementing the data thereof by 1 (S158).

Next, it is monitored whether or not the endoscope 100 is disconnected, and if it is(S160: YES), the variable Current_Scope is set to 0 to indicate no endoscope is currently connected to the processor 200 (S162). After step S162, control returns to S122 to repeat the whole procedure shown in FIGS. 4A and 4B.

As described above, the ENDOSCOPE REGISTRERATION ROUTINE registers the data of a new endoscope only when the variable Register_OK is "True", or the white balance readjustment has been required.

Further, if there isn't any available record in the endoscope database for the registration of the new endoscope, the ENDOSCOPE REGISTRATION ROUTINE selects the record having the oldest "registered date & time" and replaces the data on that record with the data obtained from the EEPROM 102 of the new endoscope. In other words, the data of the oldest endoscope and therefore supposed to be the data least variable in the endoscope database is replaced with the data of the new endoscope.

It should be noted, however, the record having the oldest "used date & times" may also be selected instead of the oldest "registered date & time". The endoscope associated with the record having the oldest "used date & time" is not used for the longest period of time among the endoscopes registered with the endoscope database. Therefore, the data of this endoscope may be less variable compared to the data of other endoscopes and therefore may be replaced with data of the new endoscope.

Figure 5:
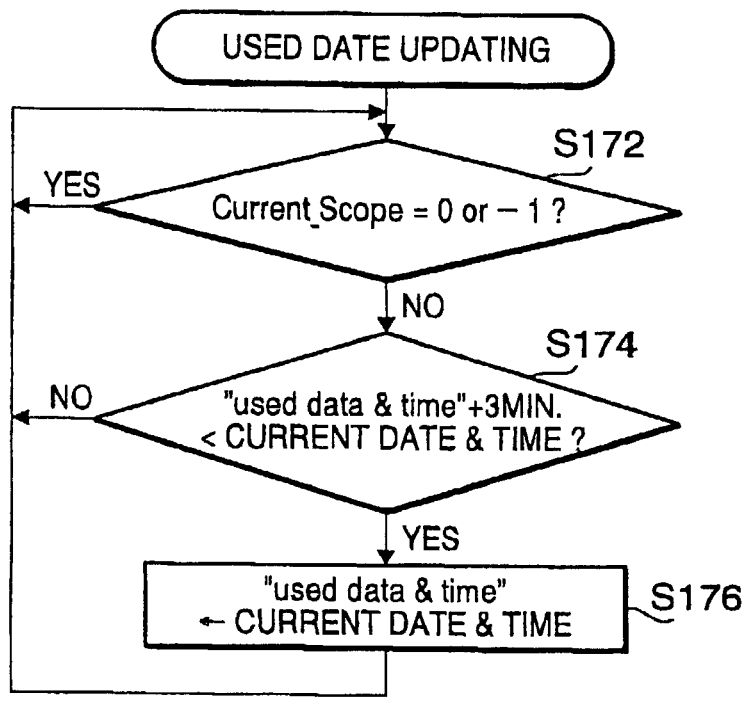
FIG. 5 shows a flow chart of the USED DATE UPDATING ROUTINE.

FIG. 5 shows a flow chart of the USED DATE UPDATING ROUTINE. In this routine, it is determined whether the variable Current_Scope is either "0" or "−1" (S172). In other words, it is determined whether or not an endoscope already registered with the database is connected to the processor 200. Step S172 is repeated until the variable Current_Scope indicates a number other than "0" and "−1" (S172: YES).

If the variable Current_Scope indicates a number other than "0" and "−1" (S172:NO), then the date and time of "used date & time" on the record of which "register no." is the same as the variable Current_Scope is compared with the current date and time obtained from the RTC 209 (S174). If the current date and time does not exceed "used date & time" for more than 3 minutes (S174:NO), for example, then control returns to step S172.

If the current date and time exceeds "used date & time" for more than 3 minutes (S174:YES), then the data of "used date & time" is replaced with the current date and time (S176), and thereafter control returns to step S172 to repeat the whole procedure.

Figure 6:
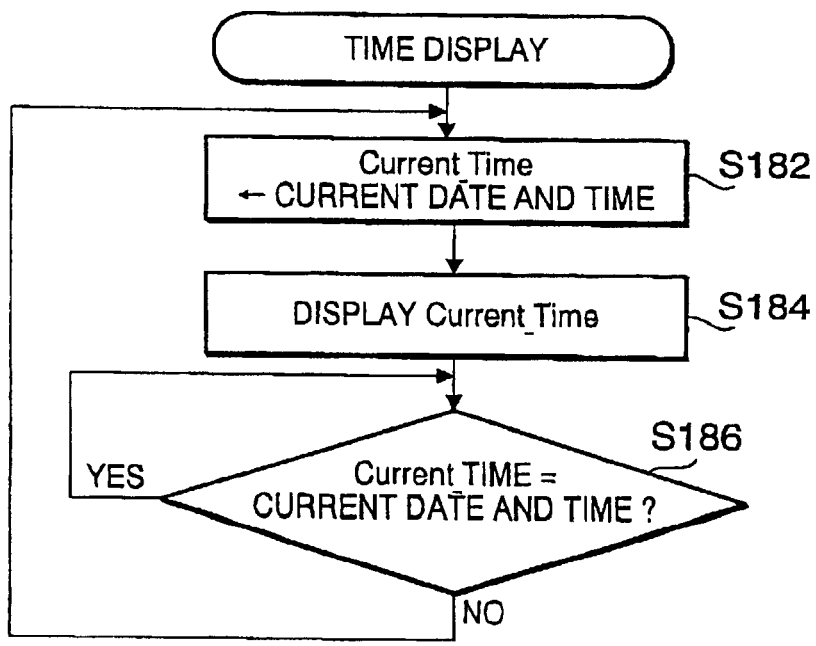
FIG. 6 shows a flow chart of the TIME DISPLAY ROUTINE.

FIG. 6 shows a flow chart of the TIME DISPLAY ROUTINE. In TIME DISPLAY ROUTINE, the CPU 201 first set a variable Current_Time to the current date and time obtained from the RTC 209 (S182).

Next, the CPU 201 controls the CRTC 206 to display the date and time indicated by the variable Current_Time on the monitor 300 (S184). The CRTC 206 generates a text information corresponding to the date and time indicated by the variable Current_Time, e.g. "Mar. 2, 2001, 15 h 20 min 10 sec", and then displays the generated text information on the monitor 300.

Next, at step S186, the variable Current_Time is compared with the current date and time obtained from the RTC 209. This step is repeated until the difference between the data held by the variable Current_Time and the current date and time reaches 1 second (S186:YES). If the difference reaches 1 second (S186:NO), then control returns to step S182 to repeat the whole procedure and thereby update the date and time displayed on the monitor 300.

Although the present invention has been described in accordance with the embodiment shown, one of ordinary skill in the art will readily recognize that there could be variations to the embodiment and those variations would be within the spirit and scope of the present invention.

Figure 7:
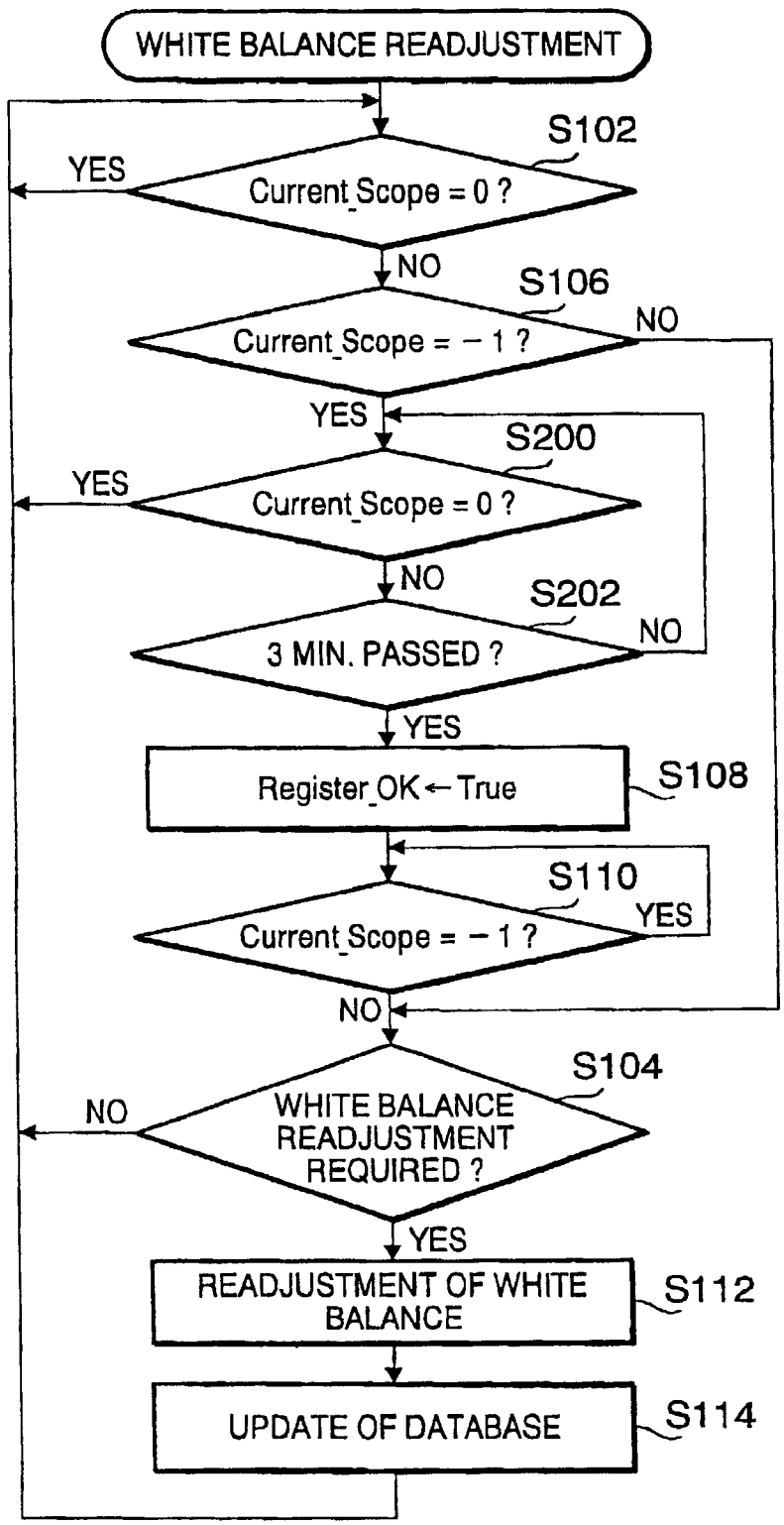
FIG. 7 shows a modified flow chart of the WHITE BALANCE READJUSTMENT ROUTINE shown in FIG. 3.

FIG. 7 shows a modified flow chart of the WHITE BALANCE READJUSTMENT ROUTINE shown in FIG. 3. In the modified routine, step S104 is moved to immediately before S112 so that whether or not the white balance readjustment is required does not affect the registration of a new endoscope with the endoscope database.

Further, new steps S200 and S202 are inserted between steps S106 and S108. Steps S200 and S202 are executed when a new endoscope is connected to the processor 200 (S106: YES). These steps determine whether a predetermined period of time, e.g., three minutes, has passed since the new endoscope has been connected to the endoscope. If the endoscope Is disconnected before the predetermined period of time has passed (S202: NO, S200: YES), then control returns to step S102 without setting the variable Register_OK to True, or allowing the registration of the new endoscope with the endoscope database.

On the contrary, if the new endoscope keeps the connected state over the predetermined period of time (S200: NO, S202: YES), then the process of the routine goes to step S108 and set the variant Register_OK to "True" (S108) to allow the ENDOSCOPE REGISTRATION ROUTINE to register the data of the new endoscope with the endoscope database.

The modified WHITE BALANCE READJUSTMENT ROUTINE mentioned above is advantageous in avoiding the registration of the data of the endoscopes with the endoscope database that are connected to the processor 200 for only a short time in order to, for example, conforming the operation of the endoscopes. Accordingly, the modified routine prevents the endoscope database from being filled up by data of a number of such temporarily connected endoscopes.

The present disclosure relates to the subject matter contained in Japanese Patent Application No. P2001-299978, filed on Sep. 28, 2001, which is expressly incorporated herein by reference in its entirety.

What is claimed is:

1. A method for registering an electronic endoscope with a database, the electronic endoscope being connectable to a processor that processes an image captured by the electronic endoscope, a plurality of electronic endoscopes being configured to be registerable with the database, the method comprising:
   determining whether or not an electronic endoscope should be registered with the database depending upon whether an operational condition of at least one of the electronic endoscope and the processor satisfies a predetermined condition when the electronic endoscope, which is not registered, is connected with the processor; and
   registering the electronic endoscope with the database when it is determined that the electronic endoscope should be registered.

2. The method according to claim 1, wherein the processor displays the image captured by the electronic endoscope on a monitor, and wherein the predetermined condition includes receipt of a requirement for executing white balance readjustment of the processor.

3. The method according to claim 2, further comprising:
   retrieving color adjustment data from the electronic endoscope;
   adjusting the white balance of the processor based on the color adjustment data; and
   readjusting the white balance of the processor by modifying the color adjustment data when the requirement for executing white balance readjustment is received.

4. The method according to claim 1, wherein the predetermined condition includes connection of the electronic endoscope with the processor for more than a predetermined period of time.

5. The method according to claim 1, wherein the database is in a memory provided to the processor.

6. The method according to claim 1, further comprising:
   selecting one of a plurality of records of the database when all records of the database are filled with data; and
   registering the electronic endoscope by replacing data of the selected record with new data related to the electronic endoscope.

7. The method according to claim 6, wherein the record associated with an endoscope first registered with the database is selected when registering the electronic endoscope.

8. The method according to claim 6, wherein the record associated with an endoscope not utilized for the longest time among endoscopes registered with the database is selected when registering the electronic endoscope.

9. An apparatus for processing an image captured by an electronic endoscope, comprising:
   a memory operable to store an endoscope database;
   a first processor that processes the image captured by the electronic endoscope; and
   a second processor that determines whether or not the electronic endoscope should be registered with the endoscope database depending upon whether an operational condition of at least one of the electronic endoscope and the first processor satisfies a predetermined condition when the electronic endoscope, which is not registered, is connected to the first processor, a plurality of electronic endoscopes configured to be registerable with said endoscope database, said second processor registering the electronic endoscope with the endoscope database when it is determined that the electronic endoscope should be registered.

10. The apparatus according to claim 9, wherein said first processor displays the image captured by the electronic endoscope on a monitor, and wherein the predetermined condition includes receipt of a requirement for executing white balance readjustment of said first processor.

11. The apparatus according to claim 10, wherein the white balance of said first processor is executed based on color adjustment data obtained from the electronic endoscope, and wherein the white balance readjustment of said first processor is executed by modifying the color adjustment data when the requirement for executing white balance readjustment is received.

12. The apparatus according to claim 9, wherein the predetermined condition includes connection of the electronic endoscope with said apparatus for more than a predetermined period of time.

13. The apparatus according to claim 9, wherein said second processor selects one of a plurality of records of said endoscope database when all records are filled with data and registers the electronic endoscope by replacing data on the selected record with new data related to the electronic endoscope.

14. The apparatus according to claim 13, wherein said second processor selects the record associated with an endoscope first registered with the electronic database when registering the electronic endoscope.

15. The method according to claim 13, wherein said second processor selects the record associated with an endoscope not utilized for the longest time among endoscopes registered with the electronic database when registering the electronic endoscope.

16. A method for registering an electronic endoscope with a database, the electronic endoscope being connectable to a processor that processes an image captured by the electronic endoscope, the method comprising:
   determining whether an operational condition of at least one of the electronic endoscope and the processor satisfies a predetermined condition when the electronic endoscope is connected with the processor;

registering the endoscope with the database when the predetermined condition is satisfied;

selecting one of a plurality of records of the database when all records of the database are filled with data; and registering the electronic endoscope by replacing data of the selected record with new data related to the electronic endoscope.

* * * * *